United States Patent
Kihara et al.

(10) Patent No.: US 10,201,896 B2
(45) Date of Patent: Feb. 12, 2019

(54) PROCESSING METHOD, OPERATION COMMAND GENERATOR, NON-TRANSITORY COMPUTER-READABLE STORAGE MEDIUM STORING PROGRAM, AND PROCESSING SYSTEM

(71) Applicant: Kabushiki Kaisha Yaskawa Denki, Kitakyushu-shi (JP)

(72) Inventors: Eiji Kihara, Kitakyushu (JP); Sakae Yamaguchi, Kitakyushu (JP); Kohei Miyauchi, Kitakyushu (JP)

(73) Assignee: KABUSHIKI KAISHA YASKAWA DENKI, Kitakyushu-shi (JP)

( * ) Notice: Subject to any disclaimer, the term of this patent is extended or adjusted under 35 U.S.C. 154(b) by 210 days.

(21) Appl. No.: 15/211,491

(22) Filed: Jul. 15, 2016

(65) Prior Publication Data
US 2017/0015000 A1    Jan. 19, 2017

(30) Foreign Application Priority Data
Jul. 17, 2015  (JP) .................................. 2015-143352

(51) Int. Cl.
*B25J 9/16*  (2006.01)
*G01N 35/00*  (2006.01)
(Continued)

(52) U.S. Cl.
CPC .......... *B25J 9/1679* (2013.01); *B25J 9/0087* (2013.01); *G01N 35/0092* (2013.01); *G01N 35/0099* (2013.01); *G01N 35/10* (2013.01); *G01N 35/1011* (2013.01); *G01N 2035/00495* (2013.01)

(58) Field of Classification Search
USPC .......................................................... 700/226
See application file for complete search history.

(56) References Cited

U.S. PATENT DOCUMENTS

2014/0106386 A1*  4/2014  Umeno .............. G01N 35/0099
                                                              435/23
2016/0145671 A1    5/2016  Umeno et al.
(Continued)

FOREIGN PATENT DOCUMENTS

JP        2013-9618 A     1/2013

OTHER PUBLICATIONS

Japanese Office Action dated Jan. 9, 2018 in Patent Application No. 2015-143352 (with English translation), 10 pages.
(Continued)

*Primary Examiner* — Kyle O Logan
(74) *Attorney, Agent, or Firm* — Oblon, McClelland, Maier & Neustadt, L.L.P.

(57) ABSTRACT

A processing method is for performing a processing with respect to a processing object in at least one field among biochemistry, biology, and biotechnology. The processing method includes transferring, using at least one arm of a robot configured to perform the processing, a container to a mover with the processing object attached on an inner surface of the container. The processing object is moved, using the mover, to a predetermined position on the inner surface of the container. The processing is performed, using a pipette mounted on the arm, with respect to the processing object at the predetermined position.

13 Claims, 8 Drawing Sheets

(51) Int. Cl.
*G01N 35/10* (2006.01)
*B25J 9/00* (2006.01)

(56) References Cited

U.S. PATENT DOCUMENTS

2017/0130189 A1* 5/2017 Sakamoto .............. C12M 23/08
2017/0137770 A1* 5/2017 Sakamoto .............. C12M 29/14

OTHER PUBLICATIONS

Office Action dated Nov. 20, 2018 in corresponding Japanese Patent Application No. 2015-143352, filed Jul. 17, 2015 (with English-language Translation), citing document previously submitted, 7 pgs.

* cited by examiner

PROCESSING METHOD, OPERATION COMMAND GENERATOR, NON-TRANSITORY COMPUTER-READABLE STORAGE MEDIUM STORING PROGRAM, AND PROCESSING SYSTEM

CROSS-REFERENCE TO RELATED APPLICATIONS

The present application claims priority under 35 U.S.C. § 119 to Japanese Patent Application No. 2015-143352, filed Jul. 17, 2015. The contents of this application are incorporated herein by reference in their entirety.

BACKGROUND

Field of the Invention

The embodiments disclosed herein relate to a processing method, an operation command generator, a non-transitory computer-readable storage medium storing a program, and a processing system.

Discussion of the Background

In the fields of biochemistry, biology, and biotechnology, obtaining repeatable and highly reliable experimental results requires preciseness throughout the procedure of individual operations that are performed with respect to processing objects. Examples of such operations include a series of examinations, culturing, and amplification (these operations will be hereinafter collectively referred to as "experiment"). The specifics of each procedure might vary depending on the processing object.

For example, a processing object in a container might be unsettled in position such as when the processing object attaches to the inner surface of the container; nevertheless, precision is still required such as in application of a particular chemical solution on the processing object. Generally, varying specifics depending on processing objects have been dealt with by the skillfulness (techniques) of operators.

SUMMARY

According to one aspect of the present disclosure, a processing method is for performing a processing with respect to a processing object in at least one field among biochemistry, biology, and biotechnology. The processing method includes transferring, using at least one arm of a robot configured to perform the processing, a container to a mover with the processing object attached on an inner surface of the container. The processing object is moved, using the mover, to a predetermined position on the inner surface of the container. The processing is performed, using a pipette mounted on the arm, with respect to the processing object at the predetermined position.

According to another aspect of the present disclosure, an operation command generator is to generate an operation command based on a plurality of processing symbols each assigned a predetermined number in a processing order and each indicating a processing to be performed with respect to at least one of a processing object and a container. The processing object is related to at least one field among biochemistry, biology, and biotechnology. The container has an inner surface on which the processing object is attached. The operation command includes an aggregate of jobs to control a control object including a robot configured to perform the processing with respect to at least one of the processing object and the container using at least one arm. The operation command generator includes an inserter configured to, when the plurality of processing symbols comprise a first processing symbol indicating a job to apply a liquid on the processing object, insert a movement job between the job indicated by the first processing symbol and a job indicated by a second processing symbol that is among the plurality of processing symbols and that is one number prior to the first processing symbol in the processing order. The movement job includes a job to move, using a mover, the processing object to a predetermined position on the inner surface of the container.

According to another aspect of the present disclosure, a non-transitory computer-readable storage medium stores a program for causing a computer to function as an operation command generator configured to generate an operation command based on a plurality of processing symbols each assigned a predetermined number in a processing order and each indicating a processing to be performed with respect to at least one of a processing object and a container. The processing object is related to at least one field among biochemistry, biology, and biotechnology. The container has an inner surface on which the processing object is attached. The operation command includes an aggregate of jobs to control a control object including a robot configured to perform the processing with respect to at least one of the processing object and the container using at least one arm. The operation command generator includes an inserter configured to, when the plurality of processing symbols comprise a first processing symbol indicating a job to apply a liquid on the processing object, insert a movement job between the job indicated by the first processing symbol and a job indicated by a second processing symbol that is among the plurality of processing symbols and that is one number prior to the first processing symbol in the processing order. The movement job includes a job to move, using a mover, the processing object to a predetermined position on the inner surface of the container.

According to the other aspect of the present disclosure, a processing system includes an operation command generator, a robot, and a robot controller. The operation command generator is configured to generate an operation command based on a plurality of processing symbols each assigned a predetermined number in a processing order and each indicating a processing to be performed with respect to at least one of a processing object and a container. The processing object is related to at least one field among biochemistry, biology, and biotechnology. The container has an inner surface on which the processing object is attached. The operation command includes an aggregate of jobs to control a control object. The operation command generator includes an inserter configured to, when the plurality of processing symbols comprise a first processing symbol indicating a job to apply a liquid on the processing object, insert a movement job between the job indicated by the first processing symbol and a job indicated by a second processing symbol that is among the plurality of processing symbols and that is one number prior to the first processing symbol in the processing order. The movement job includes a job to move, using a mover, the processing object to a predetermined position on the inner surface of the container. The robot is controllable as the control object to perform the processing with respect to the processing object using at least one arm. The robot controller is configured to control the control object based on the operation command.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

According to the inventors' knowledge and experience, if processing objects used in experiments in the fields of biochemistry, biology, and biotechnology are as small in amount as a few to several microliters (μL), the processing objects might attach to the inner surface of a container such as a micro-tube. The position where the processing objects attach might vary from experiment to experiment. This requires experimenters to have highly specialized skills. For example, in a processing to apply a liquid such as a chemical solution on a small-amount processing object, an experimenter is required to: visually check the position of the processing object attached on the inner surface of the container; position a pipette over the processing object; and make adjustments to ensure that the liquid is applied on the processing object.

Because of the highly specialized skills involved, this kind of processing has been difficult to automate, with the use of robots or other similar machines. A possible approach to overcoming this difficulty is to implement a robot system that picks up an image of the processing object and subjects the image to image processing so as to position the distal end of the pipette. This robot system, however, might involve higher costs and the image processing might provide less than satisfactory image recognition reliability.

In view of the circumstances, the inventors conducted studies in an attempt to provide a processing method, an operation command generator, a non-transitory computer-readable storage medium storing a program, and a processing system that involve simpler and less costly control to position a pipette in relation to a small-amount processing object and that enable a processing to be more reliably performed with respect to the processing object. As a result of the studies, the inventors conceived of a novel and unique processing method, a novel and unique operation command generator, a non-transitory computer-readable storage medium storing a novel and unique program, and a novel and unique processing system. Embodiments of the processing method, the operation command generator, the non-transitory computer-readable storage medium storing a program, and the processing system will be described below.

Figure 1:
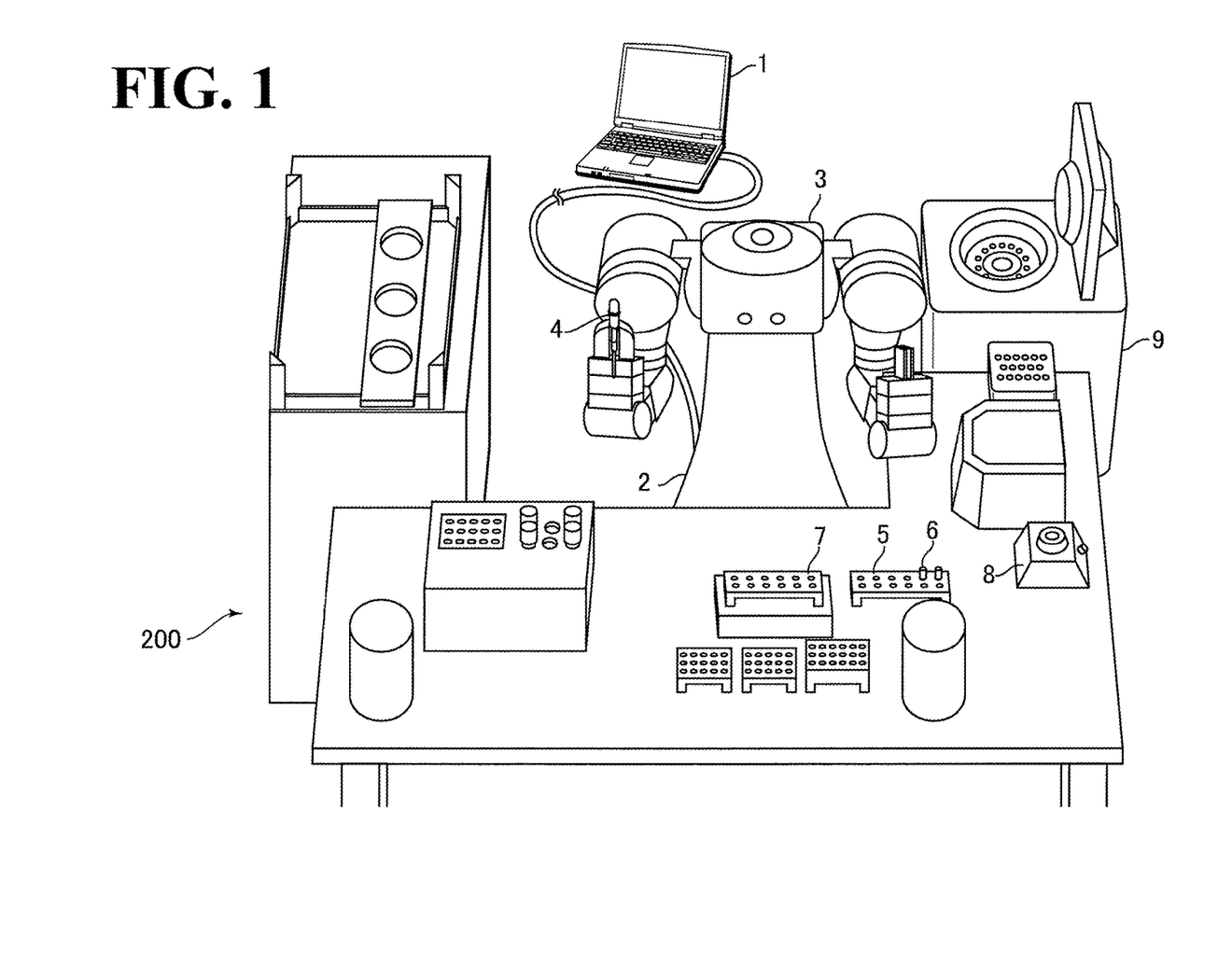
FIG. 1 schematically illustrates a physical configuration of a processing system according to an embodiment.

FIG. 1 schematically illustrates a physical configuration of a processing system 200 according to this embodiment. The processing system 200 includes an operation command generator 1. The operation command generator 1 generates an operation command based on a plurality of processing symbols. The operation command is an aggregate of jobs to control a control object. Each of the plurality of processing symbols is assigned a predetermined number in a processing order and indicates a processing to be performed with respect to at least one of a processing object and a container. The processing object is related to at least one field among biochemistry, biology, and biotechnology. The container has an inner surface on which the processing object is attached. The plurality of processing symbols are to be arranged on a protocol chart that represents a protocol. In the protocol chart, the plurality of processing symbols visually show details of the protocol. As used herein, the term protocol refers to a procedure and conditions for an operation (experiment) to be performed with respect to a processing object in the fields of biochemistry, biology, and biotechnology. Examples of the operation include, but are not limited to, a series of examinations, culturing, and amplification. The protocol is information necessary for obtaining repeatable results in an experiment and/or for verifying experiment results. In this embodiment, the operation command generator 1 is a general-purpose computer. In another possible embodiment, the operation command generator 1 may be a specialized machine. Any commercially available computer may be used as the operation command generator 1 by executing a computer program for causing the computer to function as the operation command generator 1. The computer program is typically available in the form of application software and used by being installed in a computer. The application software may be provided in the form of a recording in a CD-ROM, DVD-ROM, or any other computer-readable information recording medium. In another possible embodiment, the application software may be provided through any of various information communication networks such as the Internet. In still another possible embodiment, the application software may be implemented by what is called cloud computing, by which the application software is provided from a remote server through an information communication network.

The processing system 200 includes a robot controller 2. The robot controller 2 controls the control object based on the operation command generated by the operation command generator 1. The robot controller 2 controls a robot 3, which is one control object. The robot 3 is a multi-articular two-arm robot, which uses two robot arms (which are non-limiting examples of the arm recited in the appended claims) to perform processing with respect to the processing object. Using the robot arms, the robot 3 is capable of gripping and handling a pipette 4 and handling other laboratory instruments not illustrated. The robot 3 is also capable of moving a micro-tube 6 from a tube rack 5 to a main rack 7, which is a workspace, and to a vortex mixer 8 or a centrifuge 9. The robot 3 is also capable of moving various other containers not illustrated.

The processing system 200 according to this embodiment includes the centrifuge 9, which is a non-limiting example of the mover recited in the appended claims. The centrifuge 9 may be a typical device that effects centrifugal force to separate substances in a container utilizing a difference in specific gravity or density between the substances. In this embodiment, the centrifuge 9 is a device that rotates with the micro-tube 6 on to effect centrifugal force and move the processing object in the micro-tube 6 to a particular position, specifically, a position farther away from the axis of rotation. The use of the centrifuge 9 as the mover eliminates the need for direct contact with the processing object in moving the processing object. This eliminates or minimizes alteration in quality of the processing object due to impact on the processing object or contamination of the container by foreign matter. As a result, the processing system 200 performs experiments reliably. The mover may be any other device that is capable of moving the processing object attached on the inner surface of the container to a predetermined position on the inner surface of the container. For example, in the case of magnetic force or electrostatic force to act on the processing object, the mover may be a device that moves the processing object by magnetic force or electrostatic force.

While the embodiment illustrated in FIG. 1 includes devices such as the vortex mixer 8 and the centrifuge 9, these devices are laboratory instruments provided for exemplary purposes only; any other laboratory instruments may be provided in addition to or in place of these devices. For example, the processing system 200 may include a rack to store Petri dishes, a magnet rack, and any other laboratory instruments. While the robot 3 according to this embodiment is a two-arm robot, the processing system 200 may include one or a plurality of arms that may not necessarily be mounted on a single robot. For example, a plurality of separate robot arms may be independent of each other and controlled by the robot controller 2 to cooperate with each other.

Figure 2:
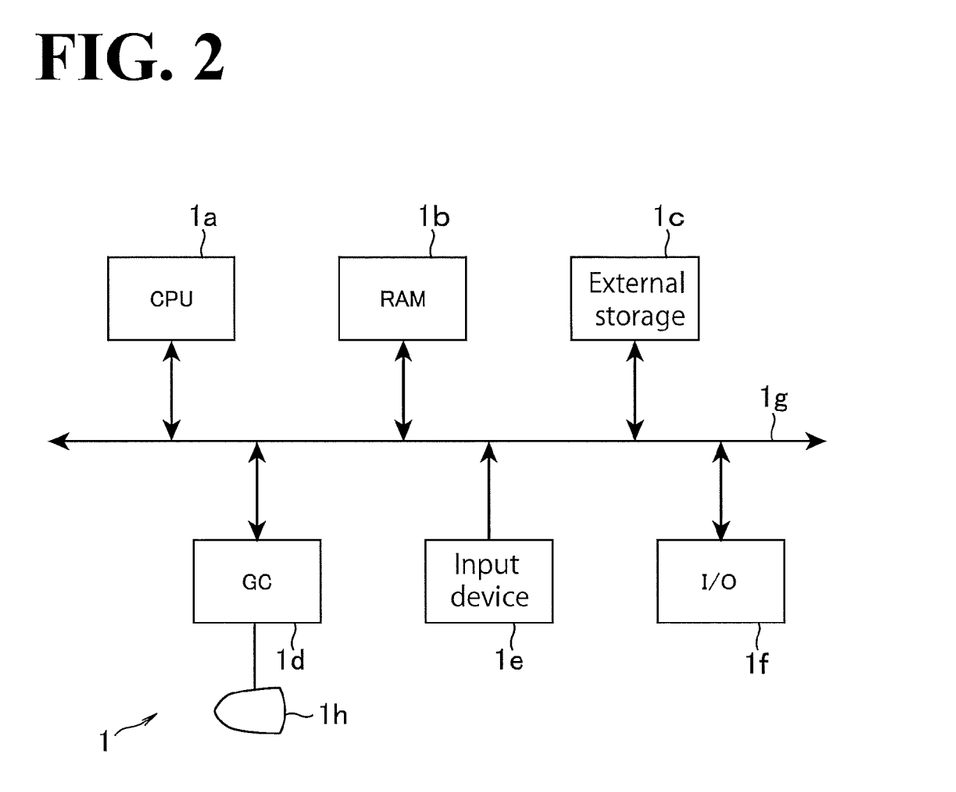
FIG. 2 is a block diagram illustrating a physical configuration of an operation command generator according to the embodiment.

FIG. 2 is a block diagram illustrating a physical configuration of the operation command generator 1 according to this embodiment. The configuration illustrated in FIG. 2 is a configuration of a general-purpose computer serving as the operation command generator 1. Specifically, a CPU (Central Processing Unit) 1a, a RAM (Random Access Memory) 1b, an external storage 1c, a GC (Graphics Controller) 1d, an input device 1e, and an I/O (Input/Output) 1f are connected with each other through a data bus 1g so that electrical signals are sendable to and from these elements. The external storage 1c is a device that statically records information, examples including, but not limited to, HDD (Hard Disk Drive) and SSD (Solid State Drive). The GC 1d outputs a signal to a monitor 1h, which is a flat panel display or a similar display that makes an image visually recognizable by a user. The monitor 1h displays an image indicated by the signal from the GC 1d. The input device 1e is a device for the user to input information, examples including, but not limited to, a keyboard, a mouse, and a touch panel. The I/O 1f is an interface for the operation command generator 1 to exchange information with external machines and devices.

Figure 3:
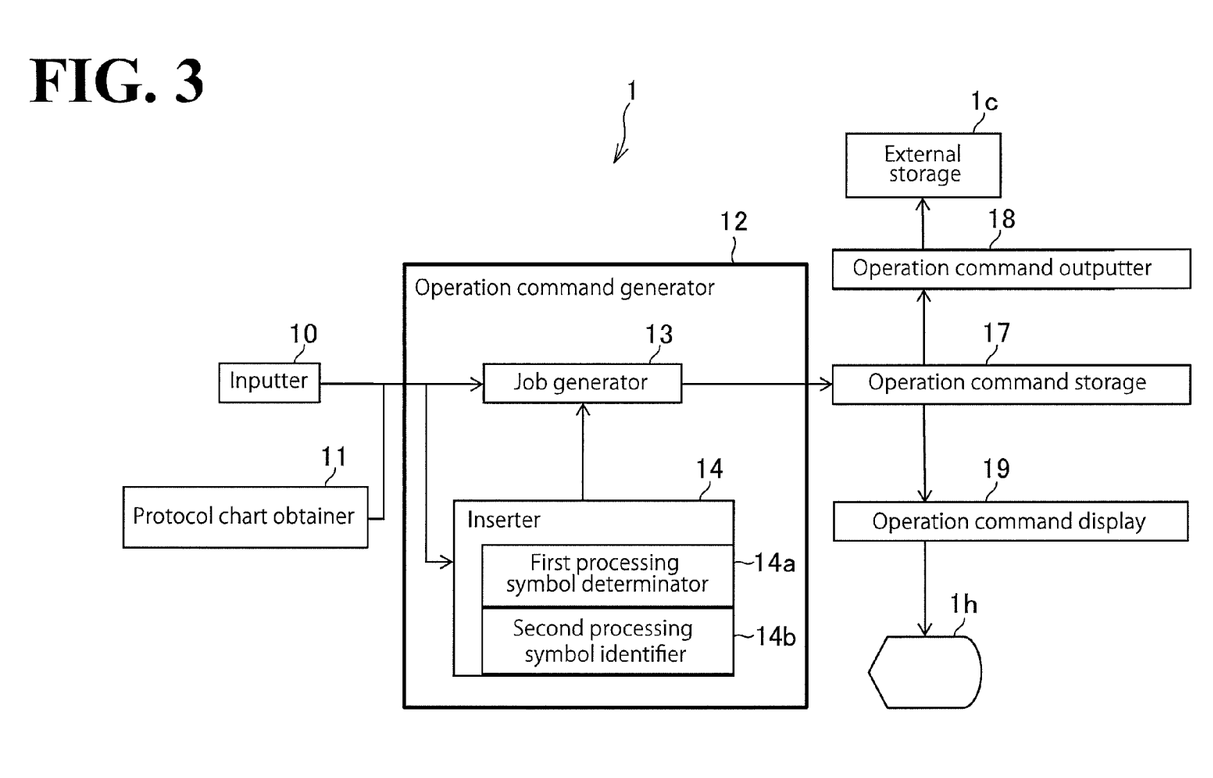
FIG. 3 is a functional block diagram of the operation command generator according to the embodiment.

FIG. 3 is a functional block diagram of the operation command generator 1 according to this embodiment. It is noted that the functional blocks shown focus on the functions of the operation command generator 1 and are not intended as requiring a physical configuration that has functional blocks corresponding one-by-one to the functional blocks shown. Some of the functional blocks may be implemented by an information processor, such as the CPU 1a, of the operation command generator 1 executing a particular kind of software or particular kinds of software. Other functional blocks may be implemented by assigning a particular storage area or particular storage areas to an information storage, such as the RAM 1b, of the operation command generator 1.

The operation command generator 1 includes an inputter 10 and a protocol chart obtainer 11. The inputter 10 receives various kinds of input from the user. The protocol chart obtainer 11 obtains a protocol chart that represents a protocol. The operation command generator 1 also includes the operation command generator 12. The operation command generator 12 generates an operation command based on the input received by the inputter 10 and based on the protocol chart obtained by the protocol chart obtainer 11. The operation command generator 1 also includes an operation command storage 17, an operation command outputter 18, and an operation command display 19. The operation command storage 17 stores electronic data of an operation command that is being generated and electronic data of a generated operation command. The operation command outputter 18 outputs the generated operation command in the form of a robot-readable electronic file. The operation command display 19 forms into shape the electronic data of the operation command stored in the operation command storage 17, and displays the shaped electronic data on the monitor 1h.

The inputter 10 is usually implemented by the input device 1e illustrated in FIG. 2. When the operation command generator 1 is an application server used in cloud computing, the inputter 10 is implemented by the I/O 1f, which receives operation information from a remote terminal handled by a user.

The operation command generator 12 includes various functional blocks to generate the operation command. The operation command generator 12 according to this embodiment includes a job generator 13. Based on the plurality of processing symbols arranged on the protocol chart, the job generator 13 generates a job to control a control object including the robot 3. This will be described in more detail later by referring to a procedure for generating the operation command. The operation command generator 12 also includes an inserter 14. The inserter 14 inserts a movement job somewhere along the processing order where the inserter 14 finds it necessary. The movement job is a job to move the processing object using the mover. The inserter 14 includes a first processing symbol determinator 14a and a second processing symbol identifier 14b. When the plurality of processing symbols include a first processing symbol indicating a job to apply a liquid on the processing object, the inserter 14 inserts the movement job, which is a job to move the processing object, between the job indicated by the first processing symbol and a job indicated by a second processing symbol. The second processing symbol is among the plurality of processing symbols and is one number prior to the first processing symbol in the processing order.

As used herein, the term operation command refers to a command that includes a single job or an aggregate of a plurality of jobs and that specifies a processing recognizable as one unit of processing to be performed with respect to the container accommodating the processing object. The operation command is generated by converting the individual symbols represented on the protocol chart into jobs, each of which is a unit of operation to be performed by the robot, and combining the converted jobs together according to the processing order in which the jobs are performed.

Figure 4:
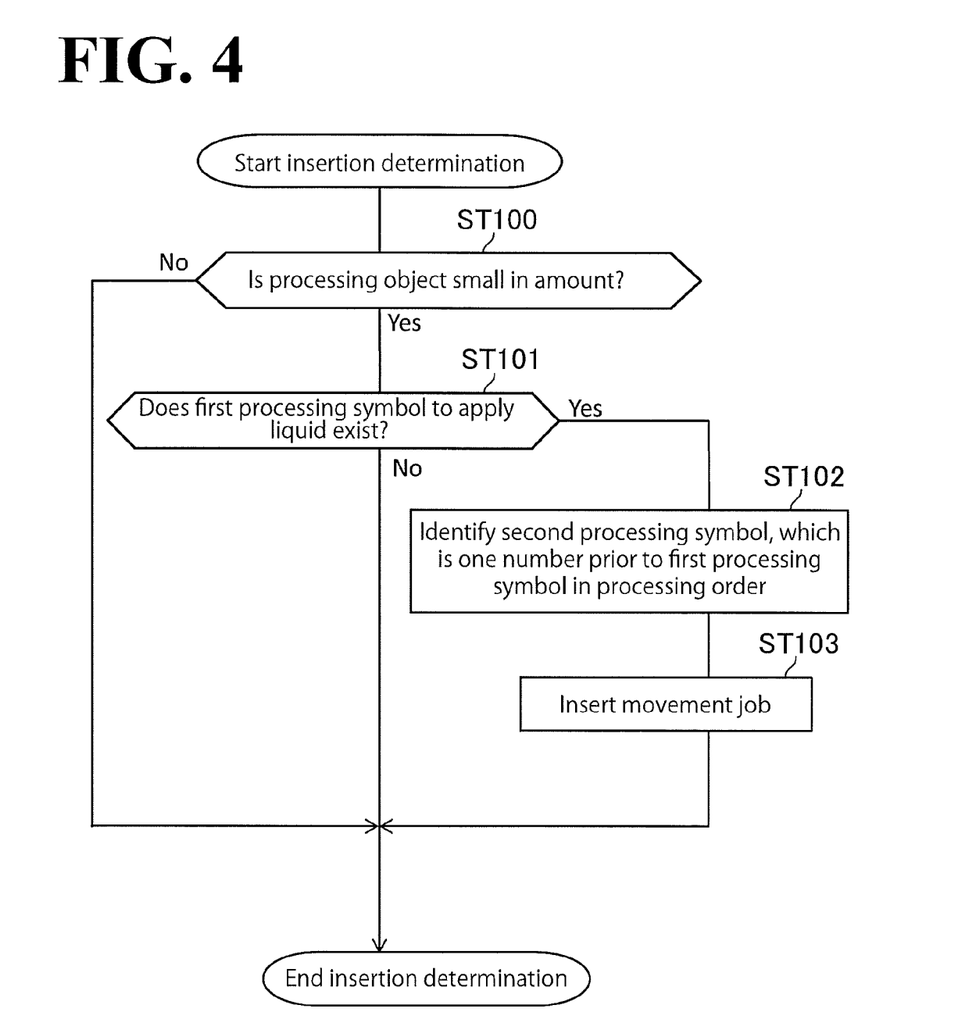
FIG. 4 is a flowchart of insertion determination processing, which is performed by an inserter of the operation command generator according to the embodiment.

FIG. 4 is a flowchart of insertion determination processing, which is performed by the inserter 14 of the operation command generator 1 according to this embodiment. After the protocol chart obtainer 11 has obtained the protocol chart, the inserter 14 determines whether the processing object is small in amount (ST 100). Specifically, the determination as to whether the processing object is small in amount may be made based on whether the actually used amount of the processing object has a volume of equal to or less than 10 μL. In another possible embodiment, the user may set a threshold.

When the actually used amount of the processing object is small in amount, the first processing symbol determinator 14a of the inserter 14 determines whether the protocol chart includes the first processing symbol, which indicates the processing to apply a liquid (ST 101). The first processing symbol is represented by the processing symbol "ADD", which indicates liquid addition processing. This will be described in more detail later by referring to FIG. 5.

When the protocol chart includes the first processing symbol, the second processing symbol identifier 14b of the inserter 14 identifies the second processing symbol, which is one number prior to the first processing symbol in the processing order (ST 102). The processing order of the plurality of processing symbols will be described in more detail later by referring to FIG. 5.

After the second processing symbol identifier 14b has identified the second processing symbol, the inserter 14 inserts the movement job, which is a job to move the processing object, between the job indicated by the first processing symbol and the job indicated by the second processing symbol (ST 103). Thus, the insertion determination processing performed by the inserter 14 ends.

Figure 5:
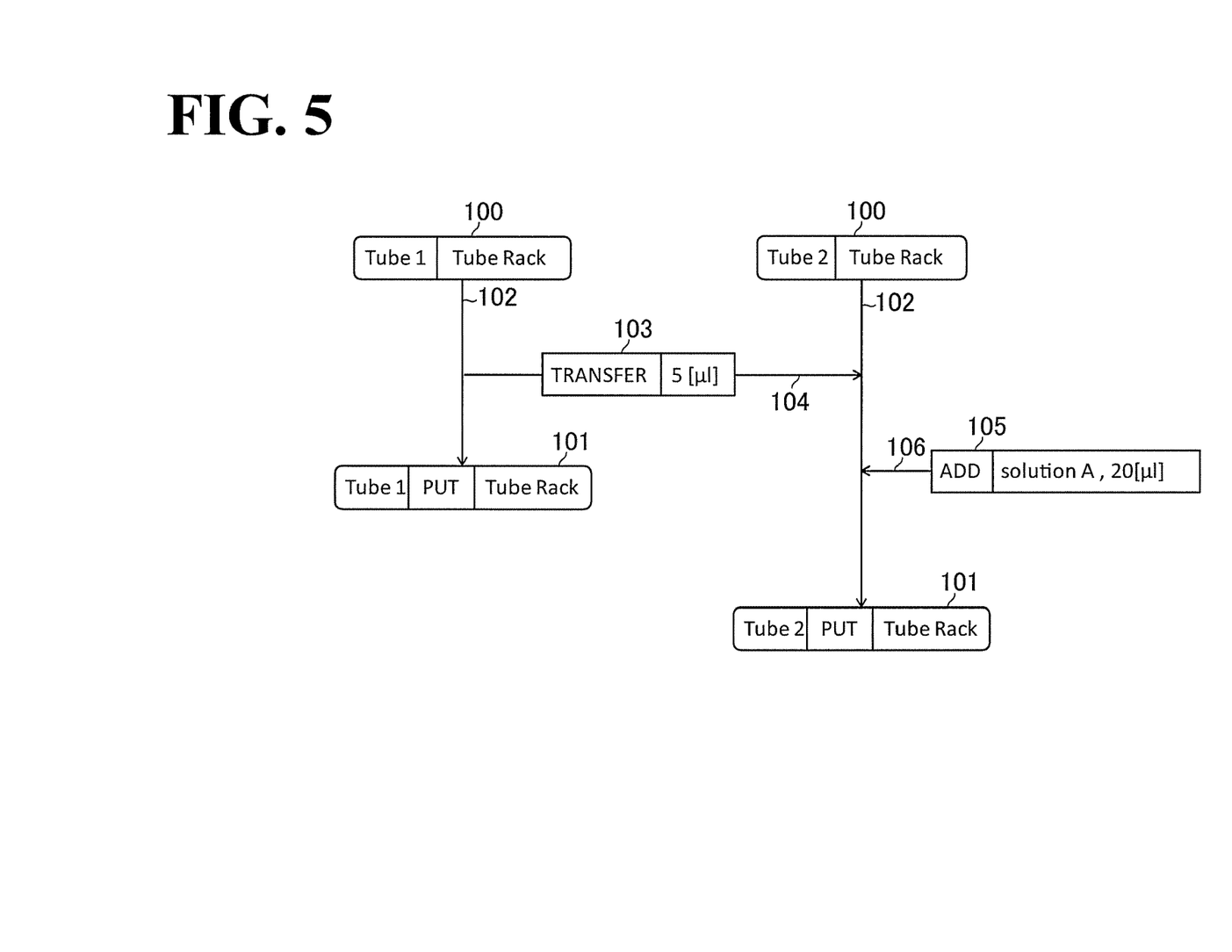
FIG. 5 illustrates an exemplary protocol chart obtained by the operation command generator according to the embodiment.

FIG. 5 illustrates an exemplary protocol chart obtained by the operation command generator 1 according to this embodiment. The exemplary protocol chart illustrated in FIG. 5 includes a first initial symbol 100 and a second initial symbol 100. The first initial symbol 100 is "Tube 1" (first micro-tube), which is accommodated in "Tube Rack" (tube rack 5). The second initial symbol 100 is "Tube 2" (second micro-tube), which is accommodated in the tube rack 5. Each initial symbol 100 indicates a processing to transfer the micro-tube 6 from the tube rack 5 to the main rack 7, which is a workspace. Each initial symbol 100 is connected through an order line 102 to a respective a final symbol 101, which indicates a processing to return the micro-tube to the tube rack 5. The processing order of the plurality of processing symbols is determined by the order line 102. In the exemplary protocol chart illustrated in FIG. 5, the processing order is a vertically descending order. For processing symbols on the same level in the vertical direction, the processing symbol further to the left is higher in the processing order, and the processing symbol further to the right is lower in the processing order.

The exemplary protocol chart illustrated in FIG. 5 includes a transfer line 104. The transfer line 104 is extending from the order line 102 of the first micro-tube to the order line 102 of the second micro-tube. The transfer line 104 carries transfer symbol 103, which is indicated "TRANSFER". The transfer symbol 103 is also indicated "5 [μL]", which indicates a job to transfer 5 [μL] of the processing object included in the first micro-tube to the second micro-tube. From the exemplary protocol chart, the inserter 14 reads 5 [μL] transfer of the processing object and determines that the actually used amount of the processing object is small.

The exemplary protocol chart also includes an addition line 106. The addition line 106 indicates a connection to the order line 102 of the second micro-tube. The addition line 106 is connected with an addition symbol 105, which is indicated "ADD". This indicates that "20 [μL]" of "Solution A" is to be added to the second micro-tube. In the exemplary protocol chart, before Solution A is added to the second micro-tube, the processing object has been transferred to the second micro-tube from the first micro-tube. The smallness in amount of the processing object requires preciseness in the positioning of the pipette over the processing object. Otherwise, "Solution A" might miss the processing object, resulting in an unexpected reaction.

The first processing symbol determinator 14a determines the addition symbol 105 as the first processing symbol, among the processing symbols included in the exemplary protocol chart. As described above, the addition symbol 105 is indicated "ADD", and the first processing symbol indicates the processing to apply a liquid on the processing object. Next, the second processing symbol identifier 14b identifies the second processing symbol, which is one number prior to the first processing symbol in the processing order. Specifically, it is the transfer symbol 103 that is one number prior to the first processing symbol, namely, the addition symbol 105, in the processing order. Therefore, the second processing symbol identifier 14b identifies the transfer symbol 103 as the second processing symbol.

Then, at the time when the job generator 13 generates the jobs indicated by the processing symbols included in the exemplary protocol chart, the inserter 14 inserts the movement job between the job to transfer the processing object as indicated by the transfer symbol 103 and the job to apply 20 [μL] Solution A on the processing object as indicated by the addition symbol 105. The movement job is a job to move the processing object using the mover, namely, the centrifuge 9. The position to which the processing object is moved is a predetermined position on the inner surface of the container, such as the micro-tube 6.

The operation command generator 1 according to this embodiment automatically inserts the movement job, which is a job to move the processing object to a predetermined position, before the job to apply a liquid on the small-amount processing object. This saves the user the need for explicitly describing the movement job on the protocol chart and ensures that the processing object is moved to a predetermined position to undergo a processing using the pipette.

Figure 6:
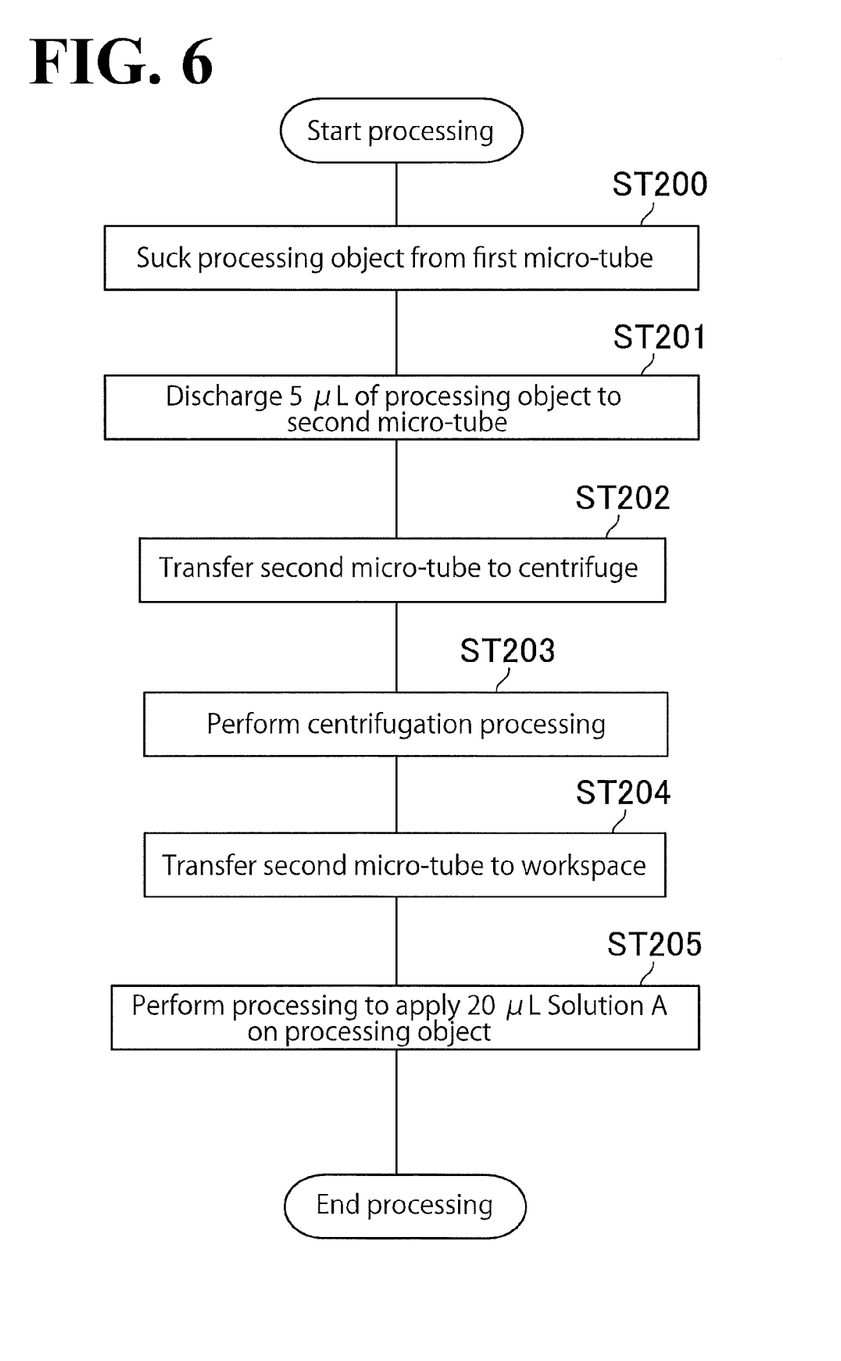
FIG. 6 is a flowchart of a processing method performed by a processing system according to the embodiment.

FIG. 6 is a flowchart of a processing method performed by the processing system 200 according to this embodiment. The flowchart illustrated in FIG. 6 is a flow of a processing method performed by the processing system 200 when the processing system 200 operates based on the operation command that has been generated by the operation command generator 1 based on the exemplary protocol chart illustrated in FIG. 5.

First, the pipette 4 gripped by one robot arm of the robot 3 performs a job to suck the processing object from the first micro-tube (ST 200). Before the job to suck the processing object, jobs to transfer the first micro-tube and the second micro-tube to the main rack 7, which is a workspace, have been performed. The job to transfer the first micro-tube to the main rack 7 is represented by the first initial symbol 100, which is indicated "Tube 1". The job to transfer the second micro-tube to the main rack 7 is represented by the second initial symbol 100, which is indicated "Tube 2".

Next, the transfer job corresponding to the transfer symbol 103 is performed. Specifically, a job to discharge 5 [μL] of the processing object sucked by the pipette 4 to the second micro-tube is performed (ST 201). Since the transfer symbol 103 has been identified as the second processing symbol as described above, the movement job is inserted between the job indicated by the transfer symbol 103 and the job indicated by the addition symbol 105, which is the first processing symbol. This causes the movement job to be performed next to the transfer job, which is a job to transfer the processing object from the first micro-tube to the second micro-tube.

In the movement job, first, one robot arm of the robot 3 grips the second micro-tube and transfers the second micro-tube to the centrifuge 9 (ST 202). The transferred second micro-tube is a container with the processing object attached on the inner surface of the container.

With the second micro-tube placed in the centrifuge 9, the centrifuge 9 performs centrifugation processing (ST 203). The centrifugation processing is a processing that utilizes centrifugal force to move the processing object to the predetermined position on the inner surface of the second micro-tube.

Then, the robot arm grips the second micro-tube and transfers the second micro-tube from the centrifuge 9 to the main rack 7, which is a workspace (ST 204). The series of processings at ST 202 to ST 204 correspond to the movement job. The movement job causes the processing object to be moved to the predetermined position on the inner surface of the container. Thus, in the processing method according to this embodiment, the movement job causes the processing object to be moved to the predetermined position. Then, the pipette is positioned over the predetermined position. This ensures reliable processing performed with respect to the processing object. The position on the inner surface of the container on which the processing object is attached might vary from experiment to experiment. Performing the movement job, however, causes the attachment position of the processing object to be settled at the predetermined position. This eliminates the need for identifying the position of the processing object by image recognition or similar processing. This, in turn, simplifies the configuration of the processing system 200 and the control of the robot 3. As a result, the automation of processings performed with respect to processing objects is facilitated. Thus, the processing method according to this embodiment enables experiments to be performed with improved preciseness at lower cost. In addition, the processing method according to this embodiment makes such experiments more highly repeatable, including the pipette processing made more reliable by the robot 3.

The processing system 200 according to this embodiment employs the centrifuge 9, which serves as the mover to move the processing object to the predetermined position. The centrifuge 9 is an instrument not only dedicated to moving processing objects but also applicable for various other purposes in experiments in the fields of biochemistry, biology, and biotechnology. That is, the use of the centrifuge 9 as the mover eliminates the need for introducing an additional new instrument in the processing system 200 and thus ensures cost reductions.

After the movement job, a processing is performed to position the pipette 4 gripped by one robot arm of the robot 3 to a predetermined position and apply 20 [µL] Solution A on the processing object (ST 205). The processing to apply the liquid in the pipette 4 on the processing object is a kind of the processing using the pipette 4 gripped by one robot arm. Other examples of the processing using the pipette 4 gripped by one robot arm include, but are not limited to, a processing to suck a small amount of the processing object using the pipette 4. In this processing, the processing object is reliably sucked by performing the movement job in advance and moving the processing object to the predetermined position.

In the processing method according to this embodiment, the processing object is moved to a predetermined position on the inner surface of the container. This eliminates the need for positioning the pipette to a different position every time a processing is performed. Instead, by positioning the processing object to the predetermined position, a liquid is reliably applied on the processing object. This improves the accuracy and reliability of experiments, resulting in improved repeatability of experiments.

Figure 7:
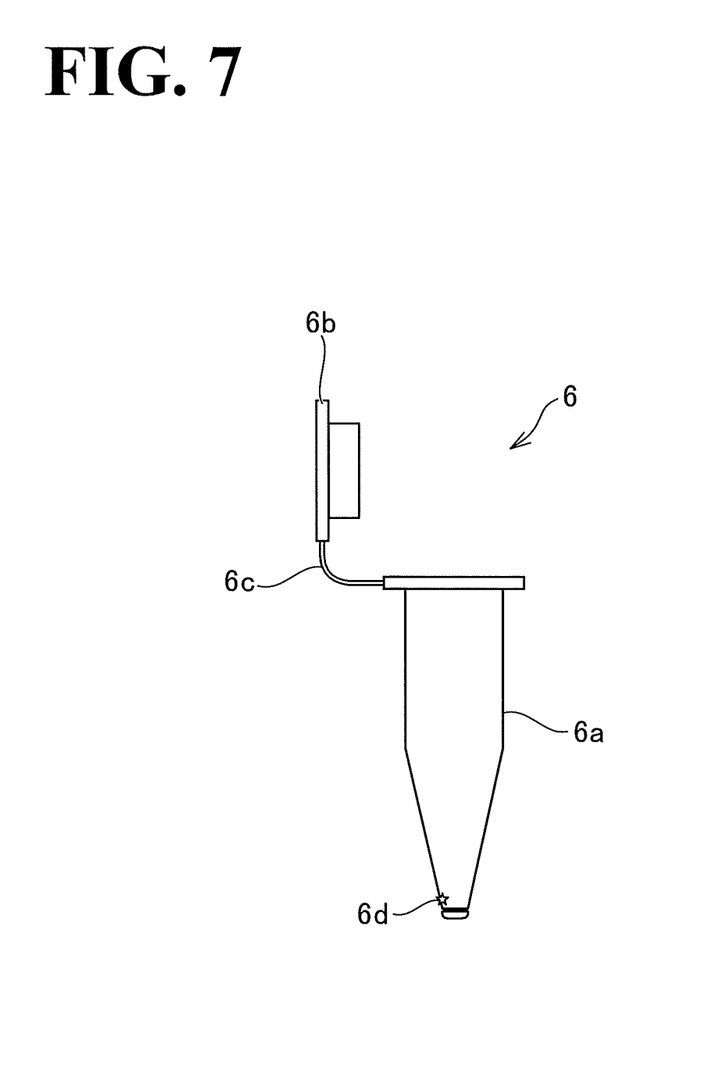
FIG. 7 illustrates a micro-tube included in the processing system according to the embodiment.

FIG. 7 illustrates the micro-tube 6, which is included in the processing system 200 according to this embodiment. The micro-tube 6 includes a receptacle 6a, a lid 6b, and a hinge 6c (which is a non-limiting example of the connection member recited in the appended claims). As illustrated in FIG. 7, legend 6d denotes a non-limiting example of the predetermined position to which the processing object is moved. The receptacle 6a is a body of the micro-tube 6, which is capable of accommodating processing objects and other substances. The lid 6b is capable of covering the opening of the receptacle 6a by being fitted in the opening, and is connected with the receptacle 6a through the hinge 6c. The hinge 6c connects the receptacle 6a and the lid 6b with each other.

The predetermined position 6d is determined in relation to the hinge 6c, which connects the receptacle 6a and the lid 6b with each other. In the embodiment shown, the predetermined position 6d is located on the inner surface of the receptacle 6a. Specifically, in a view of the micro-tube 6 from a horizontal direction with the hinge 6c in the center of the view, the hinge 6c and the predetermined position 6d, which is below the hinge 6c, form an imaginary vertical line approximately perpendicular to the horizontal direction. In other words, in a top view of the micro-tube 6 (with the lid 6b in place, covering the opening), the predetermined position 6d on the inner surface of the receptacle 6a approximately meets the hinge 6c.

In the processing method according to this embodiment, the hinge 6c, which is visually recognizable, serves as a basis for identifying the predetermined position 6d, to which the processing object is to be moved. This enables the user to more easily identify the predetermined position to which to move the processing object, even in such a situation that the micro-tube 6 is not able to be easily seen through, such as when the material of the micro-tube 6 is opaque, or even if the user has to check the experiment that the robot 3 is performing.

Figure 8:
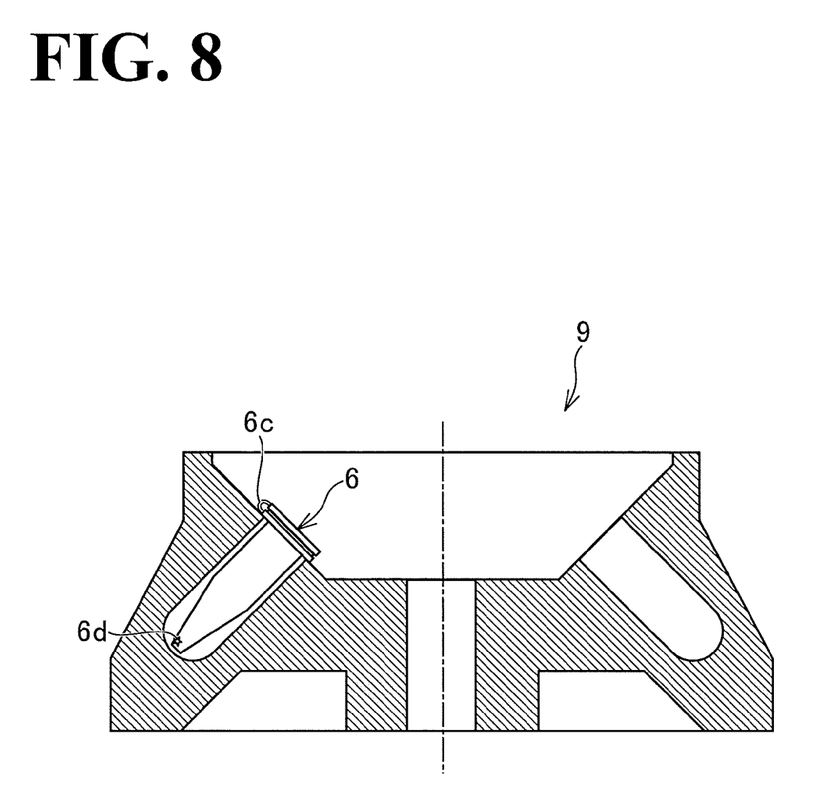
FIG. 8 illustrates the position of the micro-tube in relation to the position of a centrifuge included in the processing system according to the embodiment.

FIG. 8 illustrates the position of the micro-tube 6 in relation to the position of the centrifuge 9, which is included in the processing system 200 according to this embodiment. Technically, FIG. 8 is a cross-sectional view of the centrifuge 9 with the micro-tube 6 in place, that is, FIG. 8 is a representation of a state in which the micro-tube 6 has been set in the centrifuge 9 by the robot 3.

In the processing method according to this embodiment, one robot arm transfers the micro-tube 6, which is the container, into the centrifuge 9, which serves as the mover, with the hinge 6c at a fixed position in the centrifuge 9. In gripping the micro-tube 6, the robot 3 makes the hinge 6c oriented in a fixed direction and then sets the micro-tube 6 in the centrifuge 9 while keeping the position of the hinge 6c fixed in the centrifuge 9.

The predetermined position 6d, to which the processing object is moved, is where there is a balance between the centrifugal force of the centrifuge 9 and its weight. More specifically, in the micro-tube 6, the predetermined position 6d is farthest away from the center axis of the centrifuge 9 in the radial direction of the centrifuge 9. In this embodiment, the hinge 6c of the micro-tube 6 is oriented outward in the radial direction of the centrifuge 9 and oriented slightly upward in the vertical direction. Arranging the micro-tube 6 in this manner results in the predetermined position 6d being located on the same side as the hinge 6c on the inner surface of the micro-tube 6.

In the processing method according to this embodiment, the hinge 6c of the micro-tube 6 is orientated in a fixed direction in the centrifuge 9. This configuration facilitates identifying in advance where to move the processing object. This configuration also enables the hinge 6c to be set to any other orientation as desired so as to change where to move the processing object to where the robot 3 finds it more comfortable to perform processing with respect to the processing object.

In a situation in which the orientation of the hinge 6c of the micro-tube 6 is unsettled in the centrifuge 9, the predetermined position 6d is unsettled as well. In view of this situation, in the processing method according to this embodiment, the robot 3 detects the position of the hinge 6c in the centrifuge 9, which serves as the mover, and the robot arm(s) adjusts the position of the hinge 6c. The robot 3 may be equipped with a sensor to detect the position of the hinge 6c. A non-limiting example of the sensor is a laser detector. In another possible embodiment, a sensor such as a laser detector may be fixed on the centrifuge 9 or in the vicinity of the centrifuge 9 (for example, over the centrifuge 9) so that the robot 3 adjusts the orientation of the hinge 6c based on a result of the detection by the sensor.

In the processing method according to this embodiment, by adjusting the position of the hinge 6c, the position of the micro-tube 6 in the centrifuge 9 is corrected. This configuration prevents the processing object from being moved to an unintended position. This, in turn, improves reliability in moving the processing object to the predetermined position, and improves the accuracy and reliability of experiments.

Obviously, numerous modifications and variations of the present disclosure are possible in light of the above teachings. It is therefore to be understood that within the scope of the appended claims, the present disclosure may be practiced otherwise than as specifically described herein.

What is claimed is:

1. A method for processing a processing object of at least one of biochemistry, biology and biotechnology, comprising:
    controlling a robot comprising at least one arm such that the robot uses the at least one arm to transfer a container having a processing object on an inner surface of the container to a moving device configured to move the container based on an operation command;
    controlling the moving device to move the processing object on the inner surface of the container to a predetermined position on the inner surface of the container based on the operation command; and
    controlling the robot such that the robot delivers a liquid to the processing object at the predetermined position on the inner surface of the container based on the operation command,
    wherein the operation command comprises an aggregate of jobs to control a plurality of control objects comprising the robot and the moving device in a processing system, the operation command comprises, when the aggregate of jobs includes a job to apply the liquid on the processing object, a movement job between the job and a preceding job that is one job prior to the job to apply the liquid in a processing order such that the movement job comprises the controlling of the moving device to move the processing object to the predetermined position on the inner surface of the container.

2. The method according to claim 1, wherein the moving device is configured to apply a centrifugal force to the processing object to move the processing object to the predetermined position on the inner surface of the container.

3. The method according to claim 1, wherein the controlling of the robot to deliver the liquid comprises controlling the robot such that the robot applies the liquid to the processing object from a pipette held on the at least one arm.

4. The method according to claim 1, further comprising:
    determining the predetermined position in relation to a connection member connecting the container and a lid of the container.

5. The method according to claim 4, wherein the controlling of the robot to transfer the container comprises transferring the container to the moving device such that a position of the connection member is determined.

6. The method according to claim 4, further comprising:
    detecting a position of the connection member on the moving device; and
    adjusting the position of the connection member with the at least one arm.

7. The method according to claim 2, wherein the controlling of the robot to deliver the liquid comprises controlling the robot such that the robot applies the liquid to the processing object from a pipette held on the at least one arm.

8. The method according to claim 2, further comprising:
    determining the predetermined position in relation to a connection member connecting the container and a lid of the container.

9. The method according to claim 8, wherein the controlling of the robot to transfer the container comprises transferring the container to the moving device such that a position of the connection member is determined.

10. The method according to claim 8, further comprising:
    detecting a position of the connection member on the moving device; and
    adjusting the position of the connection member with the at least one arm.

11. The method according to claim 3, further comprising:
    determining the predetermined position in relation to a connection member connecting the container and a lid of the container.

12. The method according to claim 11, wherein the controlling of the robot to transfer the container comprises transferring the container to the moving device such that a position of the connection member is determined.

13. The method according to claim 1, further comprising:
    generating the operation command based on a plurality of processing symbols each assigned with a number in the processing order and each indicating a processing to be performed with respect to at least one of the container and the processing object,
    wherein the generating of the operation command comprises inserting, when the plurality of processing symbols comprises a processing symbol indicating the job to apply the liquid on the processing object, the movement job between the job indicated by the processing symbol and the preceding job indicated by a preceding processing symbol that is one number prior to the processing symbol in the processing order such that the movement job comprises the controlling of the moving device to move the processing object to the predetermined position on the inner surface of the container.

* * * * *